US00PP09400P

United States Patent [19]

Schumann

[11] Patent Number: Plant 9,400

[45] Date of Patent: Dec. 12, 1995

[54] GERANIUM PLANT NAMED FISCHAMPTION

[75] Inventor: Ingeborg Schumann, Albstadt, Germany

[73] Assignee: Florfis AG, Binningen, Switzerland

[21] Appl. No.: 360,345

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fischampion, particularly characterized by the combined features of orange-red flower color, large umbels with large cup-like flowers, medium to dark green foliage with medium zonation, compact to medium plant habit, and early flower response.

1 Drawing Sheet

The present invention comprises a new and distinct cultivar of geranium, botanically known as *Pelargonium, zonale* l'Hert, and hereinafter referred to by the cultivar named Fischampion.

Fischampion is a product of a planned breeding program which had the objective of creating new geranium cultivars with orange flower color and dark green foliage.

Fischampion was originated from a hybridization made by inventor Ingeborg Schumann in a controlled breeding program in Galdar, Gran Canaria, Spain in 1985. The female parent was an unnamed hybrid seedling obtained by crossing Springtime Irene, a vigorously growing cultivar having salmon pink flower color and large leaves with zonation, with a tetraploid line of the cultivar Standt Bern, which is characterized by single orange-red flowers with medium green foliage with zonation. The male parent of Fischampion was the patented variety Casino, disclosed in U.S. Plant Pat. No. 5,938, and having light red to dark salmon flower color and medium green foliage with zonation.

Fischampion was discovered and selected as one flowering plant within the progeny of the stated cross by Ingeborg Schumann in 1986 in a controlled environment in Galdar, Gran Canaria, Spain.

The first act of asexual reproduction of Fishampion was accomplished when vegetative cuttings were taken from the initial selection in February 1988 in a controlled environment in Galdar, Gran Canaria, Spain, by, or under the supervision of, Ingeborg schumann.

Horticultural examination of plants grown from these cuttings initiated in May 1988, and continuing thereafter, has demonstrated that the combination of characteristics as herein disclosed for Fischampion are firmly fixed and are retained through successive generations of asexual reproduction.

Fischampion has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fischampion, which, in combination, distinguish this geranium as a new and distinct cultivar:

1. Orange-red flower color
2. Large umbels with large, cup-like flowers

3. Medium to dark green foliage with medium zonation
4. Compact to medium plant habit
5. Early flower response Of the many commercial cultivars known to the present inventor, the most similar in comparison to Fischampion is the commercial cultivar Ecco. Reference is made to attached Chart A which compares certain characteristics of Fischampion to those same characteristics of Ecco. In general comparison to Ecco, Fischampion has a somewhat lighter flower color, more compact plant habit, and earlier flower response.

The accompanying color photographic drawing shows typical flower and foliage characteristics of Fischampion, with colors being as true as possible with illustrations of this type.

In the following description, color references are made to The Royal Horticultural Society (R.H.S.) Colour Chart. The color values were determined indoors in may from plants grown indoors in Hillscheid, Federal Republic of Germany.

Classification:

*Botanical.*—A hybrid of the species *Pelargonium zonale* l'Hert.

*Commercial.*—Zonal geranium, cv., Fischampion.

Inflorescence:

*Umbel.*—Shape: Nearly semi-spherical. Average diameter: 115 mm. Average depth: 55 mm. Peduncle length: 170 mm. Peduncle color: Light green, upper part dark red. Pedicel length: 30 mm. Pedicel color: Dark red. Number of flowers per Umbel: 20–30.

*Corolla.*—Average diameter: 52 mm. Form: Semi-double. Number of petals: 6–7. Number of petaloids: 0–1. Color (general tonality from a distance of three meters): Orange-red. Color of upper petals: 40A. Color of lower petals: 40A–B. Markings on upper petals: Very short dark red veins in the throat of the flower. Color of lower surface of petals: 41-B. Color of sepals: Green, dark red base. Number of sepals: 5.

*Bud.*—Shape: Elliptical. Color (adaxial): Green, with anthocyanin at the base. Color (abaxial): Orange-red.

*Reproductive organs.*—Androecium: 7 fertile anthers, white filaments and orange pollen. Gynoecium: 5 lobed stigma, light red style and pink stigma.

*Spring flowering response period.*—In Hillscheid, Federal Republic of Germany, in 1993 plants had on average 1.5 flowers opened 11 weeks after planting of unrooted cuttings.

*Outdoor flower production.*—The flower count in 1992 in Hillscheid, Federal Republic of Germany was about 40 flowers per plant for May through August observation period.

*Durability.*—Shatter, resistance, good.

Plant:

*Foliage.*—Form: Kidney-shaped. Margin: Bicrenated. Size of leaf: 95 mm. Color of upper surface: Medium to dark green, approximately 137B. Color (zonation): Brown, approximately 166A. Tolerance of botrytis: Average.

*General appearance and form.*—Internode length: 20–30 mm. Branching pattern: 1.7 branches per week. Height: 38 cm, (in September, based on 32-week-old plants).

CHART A

| CHARACTERISTIC | FISCHAMPION | ECCO |
|---|---|---|
| Flower color, upper petals | 40A | 43A |
| Plant height | 38 cm | 42 cm |
| Number of flowers/plant (11-week-old plants) | 1.5 | 0.8 |

It is claimed:

1. A new and distinct cultivar of geranium plant named Fischampion, as illustrated and described.

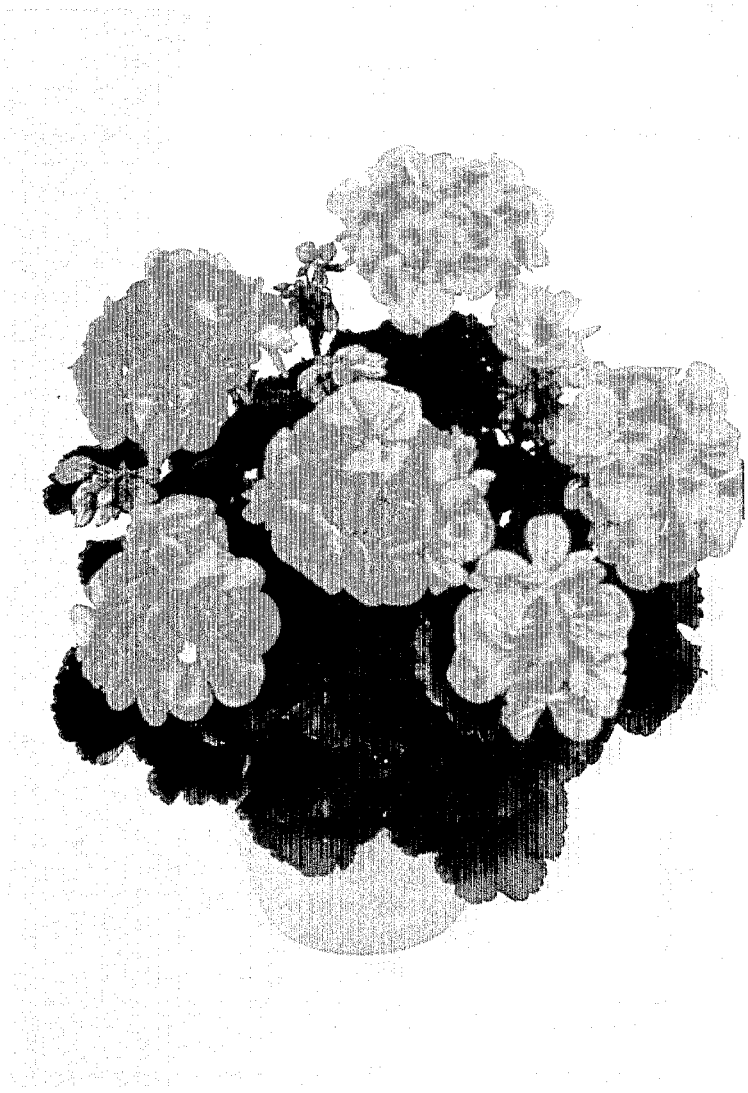

* * * * *